US008034396B2

(12) United States Patent
Kapiamba et al.

(10) Patent No.: US 8,034,396 B2
(45) Date of Patent: Oct. 11, 2011

(54) BIOADHESIVE COMPOSITION FORMED USING CLICK CHEMISTRY

(75) Inventors: Mbiya Kapiamba, Cromwell, CT (US); Nadya Belcheva, Hamden, CT (US)

(73) Assignee: Tyco Healthcare Group LP, North Haven, CT (US)

(*) Notice: Subject to any disclaimer, the term of this patent is extended or adjusted under 35 U.S.C. 154(b) by 237 days.

(21) Appl. No.: 12/368,415

(22) Filed: Feb. 10, 2009

(65) Prior Publication Data

US 2009/0247651 A1 Oct. 1, 2009

Related U.S. Application Data

(60) Provisional application No. 61/041,303, filed on Apr. 1, 2008.

(51) Int. Cl.
*B05D 1/10* (2006.01)
*A61B 17/03* (2006.01)

(52) U.S. Cl. ....... 427/2.13; 523/118; 528/319; 606/214; 606/215; 514/43; 514/93; 602/12

(58) Field of Classification Search .................. 528/319; 523/118; 606/214; 514/43, 93; 427/2.13; 602/12

See application file for complete search history.

(56) References Cited

U.S. PATENT DOCUMENTS 3,767,085 A 10/1973 Cannon et al.
4,359,049 A 11/1982 Redl et al.
4,361,055 A 11/1982 Kinson
4,538,920 A 9/1985 Drake
4,753,536 A 6/1988 Spehar et al.
4,839,345 A 6/1989 Doi et al.
4,857,403 A 8/1989 De Lucca et al.
4,874,368 A 10/1989 Miller et al.
4,880,662 A 11/1989 Habrich et al.
4,978,336 A 12/1990 Capozzi et al.
4,979,942 A 12/1990 Wolf et al.
5,368,563 A 11/1994 Lonneman et al.
5,372,585 A 12/1994 Tiefenbrun et al.
5,562,946 A 10/1996 Fofonoff et al.
5,578,662 A * 11/1996 Bennett et al. .................. 524/54
5,582,955 A 12/1996 Keana et al.
5,612,050 A 3/1997 Rowe et al.
5,911,942 A 6/1999 Fofonoff et al.
6,107,365 A 8/2000 Bertozzi et al.
6,107,453 A 8/2000 Zuccato et al.
6,451,032 B1 9/2002 Ory et al.
6,527,749 B1 3/2003 Roby et al.
6,534,611 B1 3/2003 Darling et al.
6,552,103 B1 4/2003 Bertozzi et al.
6,570,040 B2 5/2003 Saxon et al.
6,576,000 B2 6/2003 Carrison
6,881,766 B2 4/2005 Hain
7,012,126 B2 3/2006 Matsuda et al.
7,105,629 B2 9/2006 Matsuda et al.
7,122,703 B2 10/2006 Saxon et al.
7,144,976 B2 12/2006 Matsuda et al.
7,172,877 B2 2/2007 Ting
7,247,692 B2 7/2007 Laredo
7,294,357 B2 11/2007 Roby
7,371,719 B2 5/2008 Stupp et al.
7,375,234 B2 5/2008 Sharpless et al.
7,618,944 B2 11/2009 Breitenkamp et al.
7,650,588 B2 1/2010 Ivansen
7,667,012 B2 2/2010 Saxon et al.
7,807,619 B2 * 10/2010 Bertozzi et al. ................. 435/18
2002/0016003 A1 2/2002 Saxon et al.
2002/0161170 A1 10/2002 Matsuda et al.
2002/0169275 A1 11/2002 Matsuda et al.
2002/0173616 A1 11/2002 Matsuda et al.
2003/0100086 A1 5/2003 Yao et al.
2003/0135238 A1 7/2003 Milbocker
2003/0199084 A1 10/2003 Saxon et al.
2003/0205454 A1 11/2003 Hlavinka et al.
2004/0170752 A1 9/2004 Luthra et al.
2004/0185053 A1 9/2004 Govindan
2004/0209317 A1 10/2004 Ting
2005/0038472 A1 2/2005 Furst
2005/0148032 A1 7/2005 Saxon et al.
2005/0222427 A1 10/2005 Sharpless et al.
2005/0233389 A1 10/2005 Ting et al.
2006/0018948 A1 1/2006 Guire et al.
2006/0085033 A1 4/2006 Criscuolo et al.
2006/0108393 A1 5/2006 Heinrich et al.
2006/0110782 A1 5/2006 Bertozzi et al.
2006/0147963 A1 7/2006 Barone et al.
2006/0193865 A1 8/2006 Govindan
2006/0228300 A1 10/2006 Chang et al.
2006/0228357 A1 10/2006 Chang et al.
2006/0240092 A1 10/2006 Breitenkamp et al.
2006/0276658 A1 12/2006 Saxon et al.
2007/0020620 A1 1/2007 Finn et al.
2007/0037964 A1 2/2007 Saxon et al.
2007/0060658 A1 3/2007 Diaz et al.
2007/0077564 A1 4/2007 Roitman et al.
2007/0086942 A1 4/2007 Chang et al.
2007/0087001 A1 4/2007 Taylor et al.
2007/0099251 A1 5/2007 Zhang et al.
2007/0140966 A1 6/2007 Chang et al.
2007/0178133 A1 * 8/2007 Rolland ....................... 424/423
2007/0178448 A1 8/2007 Tsao et al.
2007/0190597 A1 8/2007 Agnew et al.
2007/0244265 A1 10/2007 Matyjaszewski et al.

(Continued)

FOREIGN PATENT DOCUMENTS

EP 0077098 A2 4/1983

(Continued)

OTHER PUBLICATIONS

Q. Shi, et al., "The Immobilization of Proteins on Biodegradeable Polymer Fibers via Click Chemistry", Biomaterials, 29, (2008), pp. 1118-1126.

(Continued)

*Primary Examiner* — Tae H Yoon

(57) ABSTRACT

The present disclosure provides compositions which may be utilized as adhesives or sealants in medical and surgical applications. The compositions may, in embodiments, be formed from the cycloaddition reaction of a first component possessing at least one azide group with a second component possessing at least one alkyne group.

22 Claims, 2 Drawing Sheets

U.S. PATENT DOCUMENTS

2007/0244296 A1 10/2007 Tomalia et al.
2007/0249014 A1 10/2007 Agnew et al.
2007/0254006 A1 11/2007 Loose et al.
2007/0258889 A1 11/2007 Douglas et al.
2007/0269369 A1 11/2007 Gegg et al.
2007/0272122 A1 11/2007 Lahann et al.
2007/0275387 A1 11/2007 Ju
2007/0298006 A1 12/2007 Tomalia et al.
2008/0015138 A1 1/2008 Hamilton et al.
2008/0035243 A1 2/2008 Breitenkamp et al.
2008/0038472 A1 2/2008 Suzuki et al.
2008/0045686 A1 2/2008 Meagher et al.
2008/0050731 A1 2/2008 Agnew et al.
2008/0051562 A1 2/2008 Chaikof et al.
2008/0121657 A1 5/2008 Voegele et al.
2008/0138317 A1 6/2008 Fung
2008/0160017 A1 7/2008 Baker et al.
2008/0166363 A1 7/2008 Govindan et al.
2008/0171067 A1 7/2008 Govindan et al.
2008/0187956 A1 8/2008 Carrico et al.
2008/0199736 A1 8/2008 Gadeken et al.
2008/0200628 A1 8/2008 Gadeken et al.
2008/0207913 A1 8/2008 Breitenkamp et al.
2008/0214436 A1 9/2008 Yu et al.
2008/0214801 A1 9/2008 Saxon et al.
2008/0214831 A1 9/2008 Sharpless et al.
2008/0221043 A1 9/2008 Harth et al.
2008/0241856 A1 10/2008 Wong et al.
2008/0241892 A1 10/2008 Roitman et al.
2008/0242171 A1 10/2008 Huang et al.
2008/0248126 A1 10/2008 Cheng et al.
2008/0267878 A1 10/2008 Robillard et al.
2008/0283572 A1 11/2008 Boyden et al.
2008/0311412 A1 12/2008 Fokin et al.
2009/0012457 A1 1/2009 Childers et al.
2009/0018646 A1 1/2009 Zhao
2009/0053139 A1 2/2009 Shi et al.
2009/0054619 A1 2/2009 Baker et al.
2009/0061010 A1 3/2009 Zale et al.
2009/0069561 A1 3/2009 Fokin et al.
2009/0082224 A1 3/2009 Haddleton et al.
2009/0124534 A1 5/2009 Reineke
2009/0137424 A1 5/2009 Tsao et al.
2009/0181402 A1 7/2009 Finn et al.
2009/0182151 A1 7/2009 Wu et al.
2009/0196829 A1* 8/2009 Song et al. .................. 424/9.35
2009/0202433 A1 8/2009 Chang et al.
2009/0214755 A1 8/2009 Armani et al.
2009/0220607 A1 9/2009 Kiser et al.
2009/0240030 A1 9/2009 Ju et al.
2009/0247651 A1 10/2009 Kapiamba et al.
2009/0250588 A1 10/2009 Robeson et al.
2009/0253609 A1 10/2009 Fleury et al.
2009/0259016 A1 10/2009 Johnson et al.
2009/0263468 A1 10/2009 McAnulty et al.
2009/0269277 A1 10/2009 Chang et al.
2009/0281250 A1 11/2009 DeSimone et al.
2009/0297609 A1 12/2009 Shoichet et al.
2009/0306310 A1 12/2009 Wu et al.
2009/0312363 A1 12/2009 Bradner et al.
2010/0011472 A1 1/2010 Hugel et al.
2010/0015046 A1 1/2010 Govindan et al.
2010/0021391 A1 1/2010 Douglas et al.
2010/0022481 A1* 1/2010 Wang et al. .................. 514/108
2010/0034862 A1 2/2010 Laronde et al.
2010/0047258 A1* 2/2010 Wang et al. ............... 424/178.1
2010/0048738 A1 2/2010 Fleury et al.
2010/0069578 A1 3/2010 Faust et al.
2010/0098640 A1 4/2010 Cohen et al.
2010/0121022 A1* 5/2010 Musa et al. .................. 528/319
2010/0159011 A1* 6/2010 Lian et al. .................... 424/487

FOREIGN PATENT DOCUMENTS

EP 0328050 A2 8/1989
EP 0490854 B1 9/1996
EP 1975230 A1 1/2008
EP 2090592 A1 8/2009
WO WO 00/62827 10/2000
WO WO 2004/054622 A1 7/2004
WO WO 2005/062854 A2 7/2005
WO WO 2005/079217 A2 9/2005
WO WO 2005/084180 A2 9/2005
WO WO 2005/084367 A2 9/2005
WO WO 2005/087818 A1 9/2005
WO WO 2005/113605 A1 12/2005
WO WO 2006/005046 A2 1/2006
WO WO 2006/012569 A1 2/2006
WO WO 2006/050262 A2 5/2006
WO WO 2006/065266 A2 6/2006
WO WO 2006/084202 A2 8/2006
WO WO 2006/086325 A2 8/2006
WO WO 2006/091894 A2 8/2006
WO WO 2006/107617 A2 10/2006
WO WO 2006/107786 A2 10/2006
WO WO 2006/107903 A2 10/2006
WO WO 2007/003054 A1 1/2007
WO WO 2007/041394 A2 4/2007
WO WO 2007/041451 A2 4/2007
WO WO 2007/047668 A2 4/2007
WO WO 2008/004988 A1 1/2008
WO WO 2008/013618 A1 1/2008
WO WO 2008/031525 A1 3/2008
WO WO 2008/047057 A1 4/2008
WO WO 2008/075955 A2 6/2008
WO WO 2008/077406 A2 7/2008
WO WO 2008/108736 A1 9/2008
WO WO 2008/115694 A2 9/2008
WO WO 2008/120016 A1 10/2008
WO WO 2009/029242 A1 3/2009
WO WO 2009/064696 A1 5/2009
WO WO 2009/136853 A1 11/2009
WO WO 2009/140429 A2 11/2009

OTHER PUBLICATIONS

Jérôme, et al., "Recent Advances in the Synthesis of Aliphatic Polyesters Ring-Opening Polymerization", Advanced Drug Delivery Reviews, 60, (2008), pp. 1056-1076.

Zhang, et al., "2-Azido-2-deoxycellulose: Synthesis and 1, 3-Dipolar Cycloaddition", Helvetica Chimica Acta, vol. 91, pp. 608-617 (2008).

Riva, et al., "Contribution of "Click Chemisty" to the Synthesis of Antimicrobial Aliphatic Copolyester", Polymer 49, (2008), pp. 2023-2028.

Baskin, et al., "Copper Free Click Chemistry for Dynamic In Vivo Imaging", PNAS, vol. 104, No. 43, (Oct. 23, 2007), pp. 16793-16797.

Codelli, et al., "Second Generation Difluorinated Cyclooctynes for Copper-Free Click Chemistry", J. Am. Chem. Soc., vol. 130, No. 34, (2008), pp. 11486-11493.

Sletton and Bertozzi, "A Hydrophilic Azacyclooctyne for Cu-free Click Chemistry", Org. Lett. (2008) 10(14), pp. 3097-3099.

Cazalis, et al., "C-Terminal Site-Specific PEGylation of a Truncated Thrombomodulin Mutant with Retention of Full Bioactivity", Bioconjugate Chem., 15 (2004), pp. 1005-1009.

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

LeDevedec, et al., "Separation of Chitosan Oligomers by Immobilized Metal Affinity Chromatography", J. Chromatography A., 2008, 1194(2), pp. 165-171.

Hartgerink, et al., "Pepti-amphiphile Nanofibers: A Versatile Scaffold for the Preparation of Self Assembling Materials", PNAS, 2002; 99(2), pp. 5133-5138.

Van Berkel, et al., "Metal-Free Trazole Formation as a Tool for Bioonjugation", Chem Bio Chem, 8, (2007), pp. 1504-1508.

Nottelet, et al., "Synthesis of an X-ray opaue biodegradable copolyester by chemical modification of poly (ϵ-caprolactone)", Biomaterials, 27, (2006), pp. 4948-4954.
Skierka, et al., "The Influence of Different Acids and Pepsin on the Extractability of Collagen From the Skin of Baltic Cod (*Gadus morhua*)", Food Chemisty, 105, (2007), pp. 1302-1306.
Eastoe, "The Amino Acid Composition of Mammalian Collagen and Gelatin", vol. 61, (1955), pp. 589-600.
Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.
Laughlin, et al., "In Vivo Imaging of Membrane-Associated Glycans in Developing Zebrafish", Science, 320, (2008), pp. 664-667.
Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.
Witczak et al., "A Click Chemistry Approach to Glycomimetics: Michael addition of 2,3,4,6-tetra-*O*-acetyl-1-thio-β-D-glucopyranose to 4-deoxy-1,2-*O*-isopropylident-L-*glycero*-pent-4-enopyranos-3-ulose-a convenient route to novel 4-deoxy-(1→5)-5-*C*-thiodisaccharides", Carbohydrate Research, 342, (2007), 1929-1933.
Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.
Srinivasachari, et al., "Versatile Supramolecular pDNA Vehicles via "Click Polymerization" of β-cyclodextrin with oligoethyleneamines", Biomaterials, 30, (2009), pp. 928-938.
Arora, et al., "A Novel Domino-click Approach for the Synthesis of Sugar Based Unsymmetrical bis-1,2,3-triazoles", Carbohydrate Research, 343, (2008), 139-144.
Chen, et al., "Synthesis of a $C_3$-symmetric (1→6)-*N*-acetyl-β-D-glucosamine Octadecasaccharide using Click Chemistry", Carbohydrate Research, 340, (2005), pp. 2476-2482.
Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.
Srinivasachari, et al., "Effects of Trehalose Click Polymer Length on pDNA Complex Stability and Delivery Efficacy", Biomaterials, 28, (2007), pp. 2885-2898.
Godeau, et al., Lipid-Conjugated Oligonucleotides via "Click Chemistry" Efficiently Inhibit Hepatitis C Virus Translation, J. med. Chem., 2008, 51(15), pp. 4374-4376.
Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.
Cantel, et al., "Synthesis and Conformational Analysis of a Cyclic Peptide Obtained via *i* to *i* + 4 Intramolecular Side-chain to Side-chain Azide-Alkyne 1,3-Dipolar Cycloaddition" J. Org. Chem., 2008, 73 (15), pp. 5663-5674.
Dijk, et al., "Synthesis of Peptide-Based Polymers by Microwave-Assisted Cycloaddition Backbone Polymerization, "Biomacro molecules, 2007, 8(2), pp. 327-330.
Köster, et al., "Spectroscopic and Electrochemical Studies of Ferroceryl Triazole Amino Acid and Peptide Bioconjugates Synthesized by Click Chemisty", Organometallics, 2008, 27(23) pp. 6326-6332.
Dijk, et al., "Synthesis and Characterization of Biodegradable Peptide-Baed Polymers Prepared by Microwave-Assisted Click Chemisty", Biomacromolecules, 2008, 9(10), pp. 2834-2843.
Jiang, et al., "Amphiphilic PEG/alkyl-grafted comb polylactides", J. Polymer Science Part B: Polymer Physics, 45(22), 2007, pp. 5227-5236.
Ochs, et al., "Low-Fouling, Biofunctionalized, and Biodegradeable Click Capsules", Biomacromolecules, 2008, 9(12), pp. 3389-3396.
Beatty and Tirrell, "Two-color Labeling of Temporally Defined Protein Populations in Mammalian Cells", Bioorg. Med. Chem. Lett., 18 (2008), pp. 5995-5999.

* cited by examiner

BIOADHESIVE COMPOSITION FORMED USING CLICK CHEMISTRY

CROSS-REFERENCE TO RELATED APPLICATIONS

This application claims the benefit of and priority to U.S. Provisional Patent Application No. 61/041,303, filed Apr. 1, 2008, the entire disclosure of which is incorporated by reference herein.

TECHNICAL FIELD

The present disclosure relates to compositions suitable for application in situ, including for use as tissue adhesives and/or tissue sealants.

DESCRIPTION OF THE RELATED ART

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, cyanoacrylate adhesives can have a high flexural modulus which can limit their usefulness. Another type of tissue sealant that is currently available utilizes components derived from bovine and/or human sources. For example, fibrin sealants are available. However, as with any natural material, variability in the material can be observed.

It would be desirable to provide a fully synthetic biological adhesive or sealant that is flexible, biocompatible and nontoxic.

SUMMARY

The present disclosure provides compositions suitable for use as adhesives or sealants in medical and surgical applications. The compositions may, in embodiments, be formed from the cycloaddition reaction of a first component possessing at least one azide group with a second component possessing at least one alkyne group.

Methods for utilizing these compositions to adhere and/or seal tissue are also provided. In embodiments, methods for adhering and/or sealing tissue in accordance with the present disclosure may include contacting a first component possessing at least two alkyne groups with a second component possessing at least two azide groups, catalyzing a polymerization of the first component and the second component to form a bioadhesive composition, and contacting the bioadhesive composition to at least one tissue surface so that the bioadhesive composition adheres to the at least one tissue surface. In embodiments, a composition of the present disclosure may be utilized to adhere a device, such as an implant, to tissue. In other embodiments, compositions of the present disclosure may possess a bioactive agent and thus may be utilized to deliver the bioactive agent in vivo.

BRIEF DESCRIPTION OF THE FIGURES

Various embodiments of the present disclosure will be described herein below with reference to the figures wherein.

DETAILED DESCRIPTION

Figure 1:
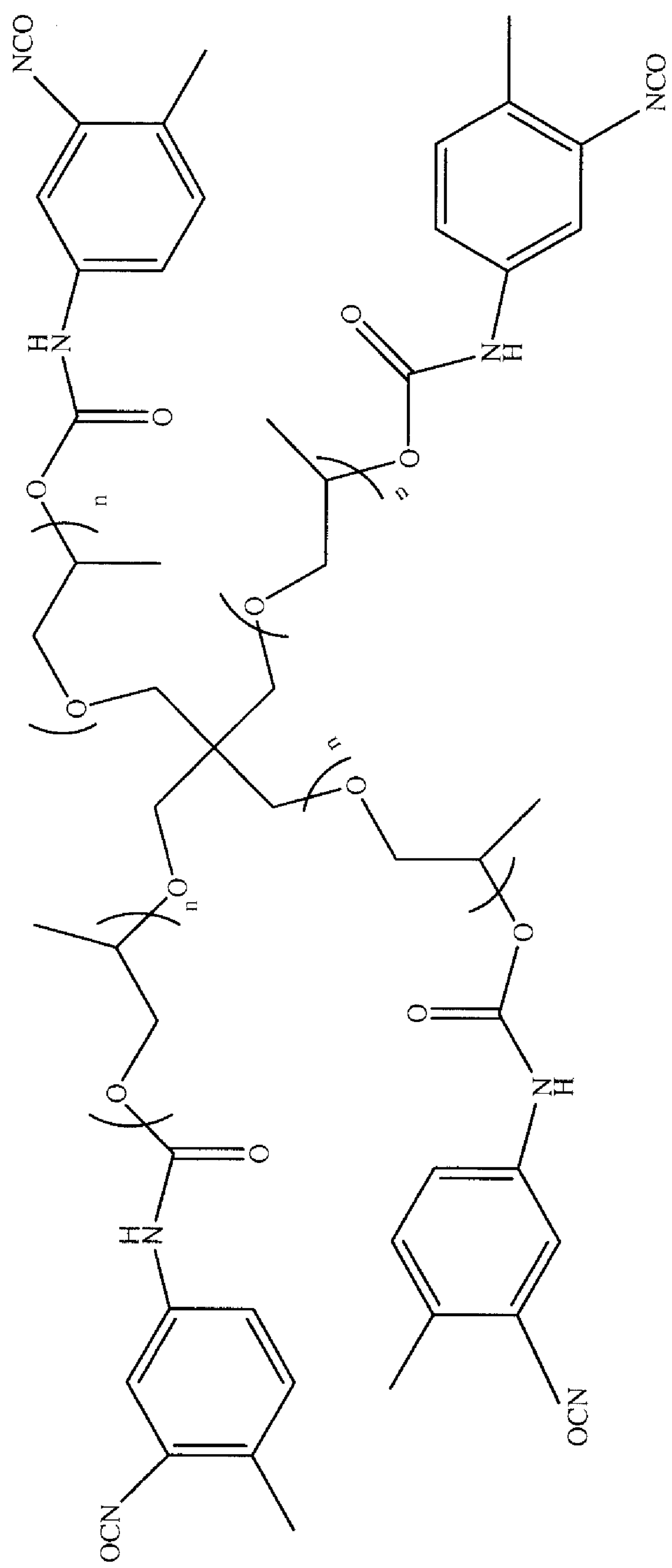
FIG. 1 is a depiction of a pentaerythritol adduct which may be utilized to form an acetylenic derivative for use in forming a bioadhesive composition of the present disclosure.

The present disclosure provides compositions which may be produced by a copper-catalyzed cycloaddition of a first component possessing at least one azide group with a second component possessing at least one alkyne group. In embodiments, the second component may possess at least one acetylene group as the at least one alkyne group. The mechanism by which the azide group and alkyne group react may be referred to, in embodiments, as click chemistry. As used herein, "click chemistry" refers to a collection of supremely reliable and self-directed organic reactions, including the copper catalyzed azide-alkyne cycloaddition reaction described above, which is capable of forming a highly reliable molecular connection in water.

In embodiments, the first component, the second component, or both, may possess a core functionalized with at least two azide groups or at least two alkyne groups, in embodiments acetylenic groups, respectively. Suitable components for use as the core(s) include, but are not limited to, monomers, oligomers, macromers, polymers, and the like. In embodiments, the first component, the second component, or both may have at least 2 functional groups, in embodiments from about 3 to about 15 functional groups. These functional groups may form arms extending from the core(s). Such cores may thus be linear, branched, star-shape, dendrimeric, and the like.

In embodiments, suitable cores for use as the first component, the second component, or both, may be prepared from a polyol, a polyamine, or a polythiol. In embodiments a polyol may be used to form a core. Examples of such polyols include, in embodiments, polyethers, polyesters, polyether-esters, polyalkanols, combinations thereof, and the like.

Suitable polyethers which may be utilized in forming the core of the first component and/or the second component are within the purview of those skilled in the art and include, for example, polyethylene glycol, polypropylene glycol, polybutylene glycol, polytetramethylene glycol, polyhexamethylene glycol, copolymers thereof such as cyclodextrin-polyethylene glycols, polyacetals, and combinations thereof. In embodiments a suitable polyether may include polyethylene glycol.

Suitable polyesters which may be utilized in forming the core of the first component and/or the second component are within the purview of those skilled in the art and include, for example, trimethylene carbonate, ϵ-caprolactone, p-dioxanone, glycolide, lactide, 1,5-dioxepan-2-one, polybutylene adipate, polyethylene adipate, polyethylene terephthalate, and combinations thereof.

In addition, as noted above, the first component and/or the second component may include a poly(ether-ester) block. Any suitable poly(ether-ester) block within the purview of those skilled in the art may be utilized. These macromers may include an aliphatic diacid, aromatic diacid, alicyclic diacid, or combinations thereof, linking two dihydroxy compounds (sometimes referred to herein as a "poly(ether-ester) macromer"). Up to ten repeats of the poly(ether-ester) macromer may be present.

Suitable diacids which may be utilized in forming the poly(ether-ester) macromer include, for example, diacids having from about 2 to about 10 carbon atoms. Suitable diacids include, but are not limited to, sebacic acid, azelaic acid, suberic acid, pimelic acid, adipic acid, glutaric acid, succinic acid, malonic acid, oxalic acid, terephthalic acid, cyclohexane dicarboxylic acid, and combinations thereof.

Suitable dihydroxy compounds which may be utilized in forming the poly(ether-ester) macromer include, for example, polyols including polyalkylene oxides, polyvinyl alcohols, polycaprolactone diols, and the like. In some embodiments, the dihydroxy compounds can be a polyalkylene oxide such as polyethylene oxide ("PEO"), polypropylene oxide ("PPO"), block or random copolymers of polyethylene oxide (PEO) and polypropylene oxide (PPO), and combinations thereof.

In one embodiment, a polyethylene glycol ("PEG") may be utilized as the dihydroxy compound. It may be desirable to utilize a PEG with a molecular weight of from about 200 g/mol to about 10000 g/mol, in embodiments from about 400 g/mol to about 900 g/mol. Suitable PEGs include those commercially available from a variety of sources under the designations PEG 200, PEG 400, PEG 600 and PEG 900.

Any method may be used to form the poly(ether-ester) macromer. In some embodiments, the poly(ether-ester) macromer may be formed by combining adipoyl chloride with a PEG such as PEG 600 and pyridine in a suitable solvent, such as tetrahydrofuran (THF). The solution may be held at a suitable temperature, from about −70° C. to about 25° C., for a period of time of from about 4 hours to about 18 hours, after which the reaction mixture may be filtered to remove the precipitated pyridine hydrochloride by-product and the resulting poly(ether-ester) macromer, here a PEG/adipate compound. The resulting poly(ether-ester) macromer may be obtained from the solution by the addition of an ether or petroleum ether, and collected by suitable means which can include filtration. Other methods suitable for producing such macromers are within the purview of those skilled in the art.

In embodiments, components utilized in forming poly (ether-esters) may be functionalized and reacted to form poly (ether-ester-urethanes), poly(ether-ester-ureas), and the like.

Other examples of suitable poly(ether-ester) blocks which may be utilized include, but are not limited to, polyethylene glycol-polycaprolactone, polyethylene glycol-polylactide, polyethylene glycol-polyglycolide, and various combinations of the individual polyethers and polyesters described herein. Additional examples of suitable poly(ether-ester) blocks include those disclosed in U.S. Pat. No. 5,578,662 and U.S. Patent Application No. 2003/0135238, the entire disclosures of each of which are incorporated by reference herein.

In embodiments, the resulting poly(ether-ester) macromer may be of the following formula:

$$HO—(X-A)_y-X—OH \quad (I)$$

wherein A is a group derived from an aliphatic, aromatic, or alicyclic diacid; X can be the same or different at each occurrence and may include a group derived from a dihydroxy compound; and y may be from about 1 to about 10. In some embodiments, the A group can be derived from adipic acid, and X can be derived from a polyethylene glycol having a molecular weight of from about 200 g/mol to about 1000 g/mol, in embodiments from about 400 g/mol to about 800 g/mol, in embodiments about 600 g/mol.

The molecular weight and viscosity of these compounds may depend on a number of factors such as the particular diacid used, the particular dihydroxy compound used, and the number of repeat units present. Generally, the viscosity of these compounds may be from about 300 to about 10,000 cP at 25° C. and a shear rate of 20.25 $sec^{-1}$.

In other embodiments, polyrotaxanes may be utilized as the core of the first component, the second component, or both. Polyrotaxane materials include cyclic molecules, linear molecules threaded through the cyclic molecules, and optionally bulky end groups on the linear molecules to prevent the loss of the cyclic molecules by dethreading. With respect to rotaxanes, "linear molecules" refers to any suitable molecules, whether branched or unbranched, that are capable of threading the cyclic molecules to form the rotaxane material. The linear molecules are generally in the form of chains that are unbranched. Branching of the linear molecules may occur, but not to the extent that the branching significantly interferes with the formation of the rotaxane material.

Examples of suitable polyrotaxanes include those created by linear polymers such as poly(ethylene oxide) (PEO) penetrating the inner cavity of cyclodextrins (CDs) to form inclusion complexes with a necklace-like supramolecular structure.

In addition to the polyols described above, in embodiments a polyamine and/or a polythiol may be used to form a core.

In embodiments, the polyol, such as a polyether, polyester, or polyether-ester as described above, may be a branched polyol. Such a polyol may have a central core from which from about 3 to about 12 arms may extend, with hydroxyl groups at the free terminal of each arm. Thus, for example, a 4-armed polyol may have the following structure:

(II)

OH
OH～～～OH
OH

In embodiments, the polyol, such as a polyether, polyester, or polyether-ester as described above, may be endcapped with functional groups. Methods for endcapping the polyol to provide a reactive end group are within the purview of those skilled in the art. In embodiments, the first component may be endcapped with at least two azide groups and the second component may be endcapped with at least two alkyne groups. Where one of the components is endcapped with two groups, the other component may be endcapped with 3 or more groups.

An example of a 4-armed alkyne includes an alkyne of the following formula:

(III)

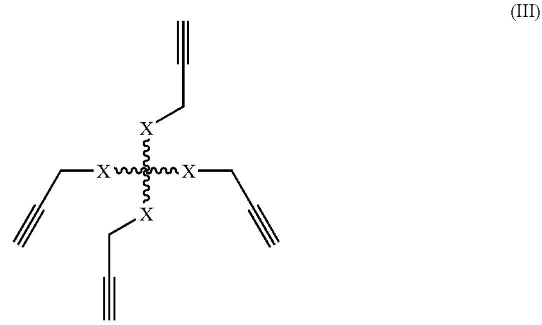

wherein X may be O, NH, S, $SO_2$, combinations thereof, and the like.

The above alkyne of formula III may be reacted with a polyazide. Suitable azides include, for example, (IV)

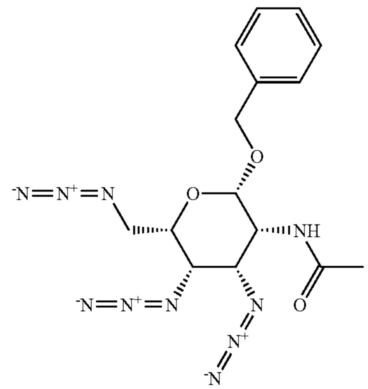

N-((2S,3R,4S,5S,6S)-4,5diazido-6-(azidomethyl)-2-(benzyloxy)tetrahydro-2H-pyran-3-yl) acetamide (V)

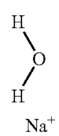

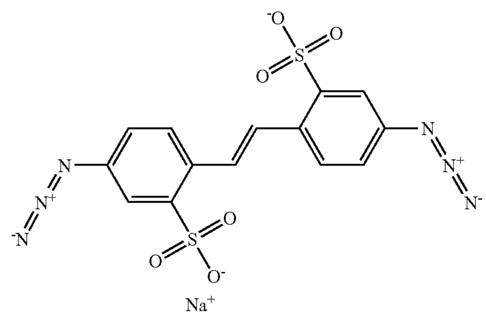

4,4'-Diazido-2,2'-stilbenedisulfonic acid disodium salt hydrate (VI)

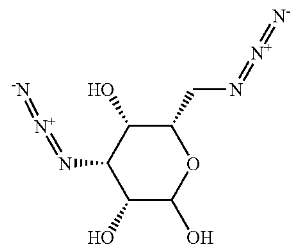

(3R,4R,5S,6S)-4-azido-6-(azidomethyl)tetrahydro-2H-pyran-2,3,5-triol (VII)

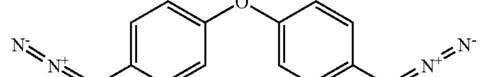

4,4'-oxybis(azidobenzene)

(VIII)

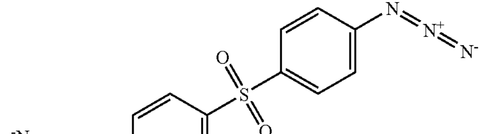

4,4'-sulfonylbis(azidobenzene)

(IX)

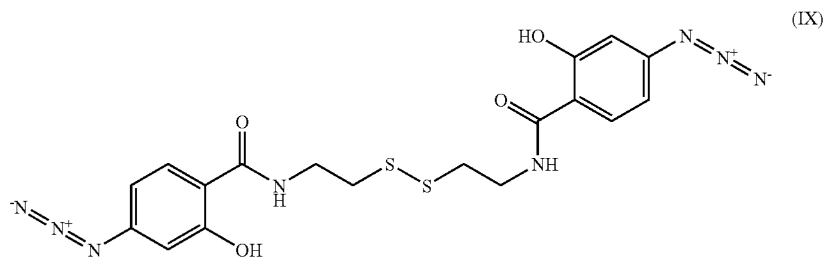

bis[2-(4-azidosalicylamido)ethyl]disulfide (X)

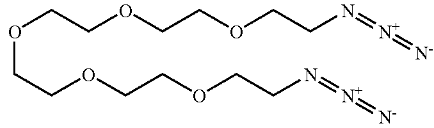

1,17-diazido-3,6,9,12,15-pentaoxaheptadecane (XI)

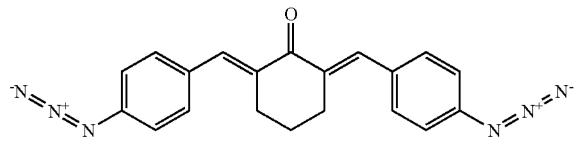

(2E,6E)-2,6-bis(4-azidobenzylidene)cyclohexanone (XII)

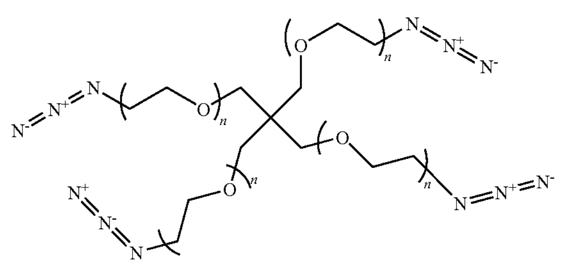

tetraazido-pentaerythritol ethoxylate heptakis-6-azido-6-deoxy-beta-cyclodextrin, combinations thereof, and the like. The alkyne of formula III may be reacted with an azide utilizing a copper catalyst to produce a compound of the present disclosure having the following structure:

(XIII)

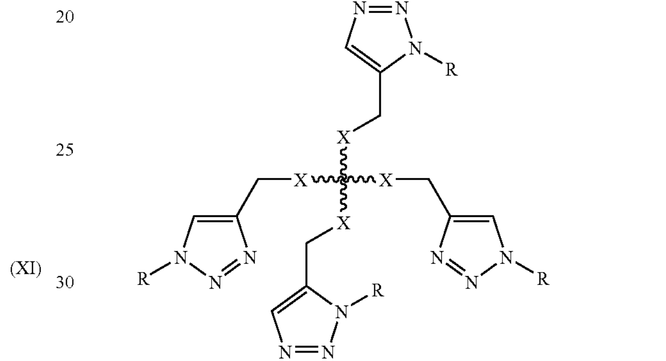

wherein X is as defined above for formula III and R may be the remainder of the polyazide component, i.e., a fragment of a polyazide molecule wherein the azide group is linked to the rest of the molecule through an alkyl group, alicyclic group, aromatic group, combinations thereof, and the like.

In other embodiments, a branched alkyne may be of the following formula (XIV)

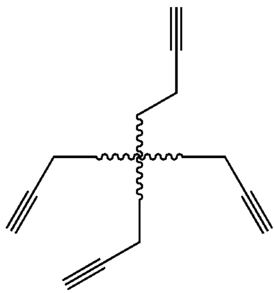

Other branched alkynes include, for example,
(XV)
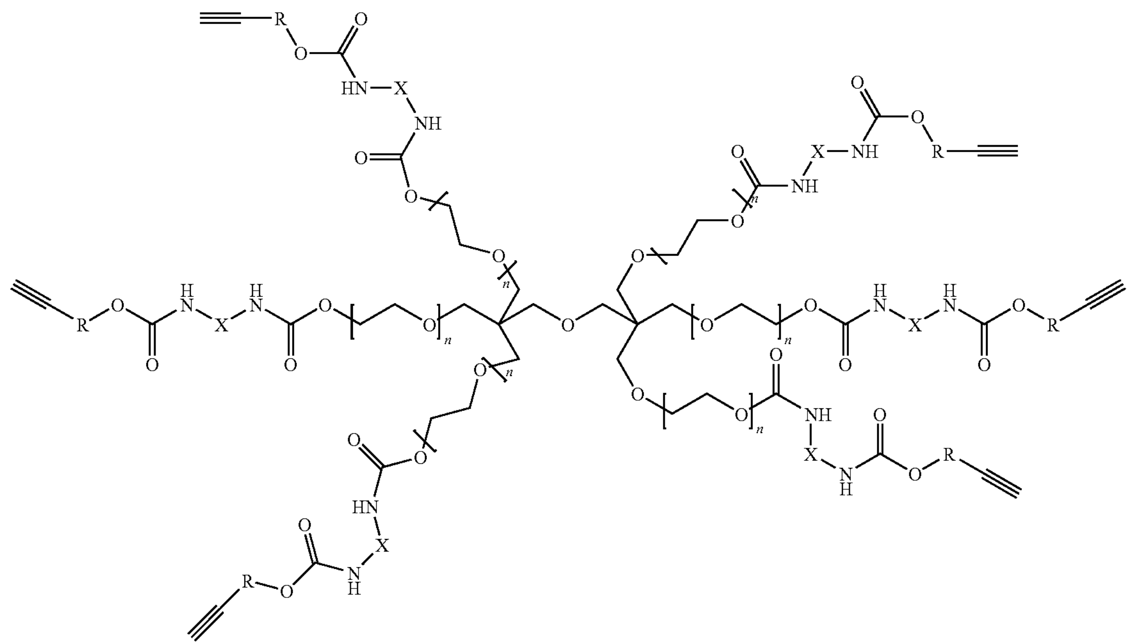
wherein X may be aliphatic, alicyclic, aromatic, or a combination thereof, and
wherein R may be aliphatic, alicyclic, aromatic, or a combination thereof;
wherein Y may be aliphatic, alicyclic, aromatic, or a combination thereof, and
wherein R may be aliphatic, alicyclic, aromatic, or a combination thereof; and
(XVI)
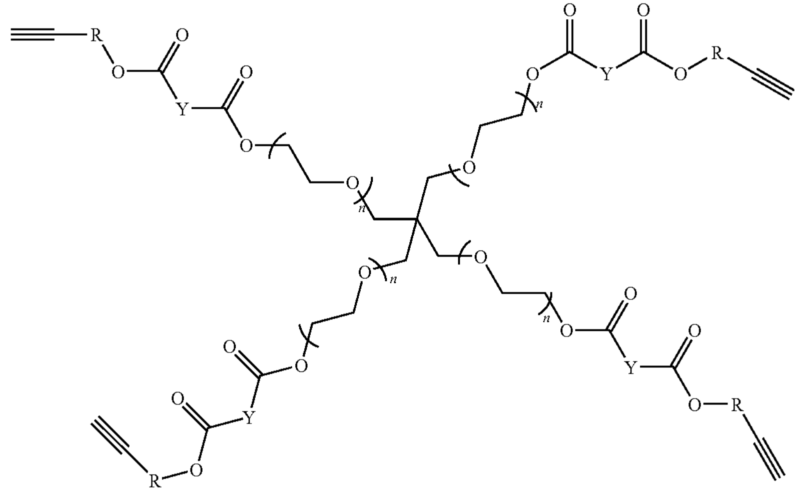

(XVII)

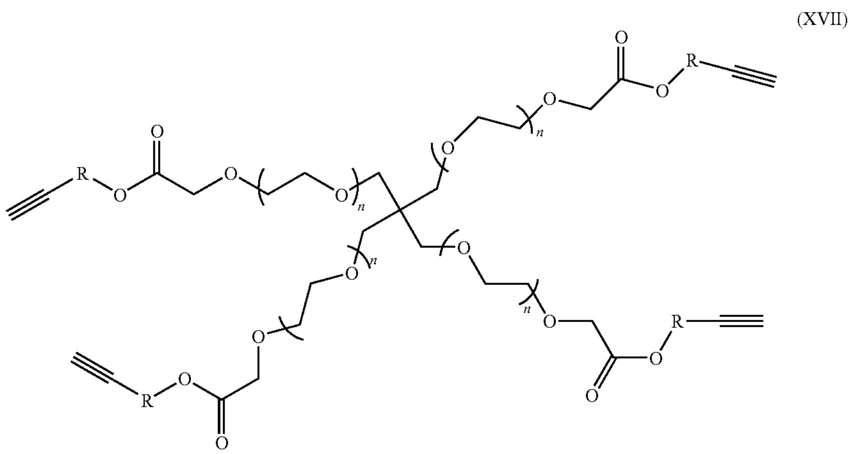

wherein R may be aliphatic, alicyclic, aromatic, or a combination thereof, and n in any of the formulas above may be a number from about 0 to about 112, in embodiments from about 1 to about 100, in other embodiments from about 3 to about 56.

A branched azide may have from about 3 to about 12 arms, in embodiments from about 4 to about 6 arms. An exemplary 4-armed branched azide may have the following generic formula (XVIII)

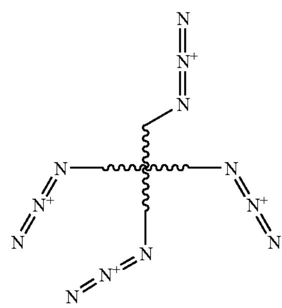

The alkyne of formula V and the azide of formula VI may then be reacted in the presence of a copper catalyst to produce the following compound:

(XIX)

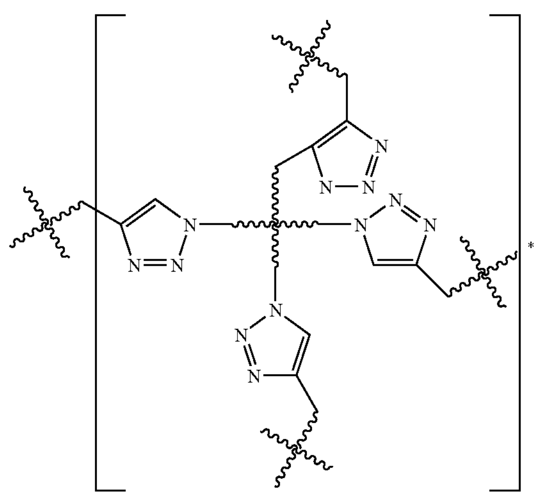

The use of copper catalysts, in embodiments Cu(I) catalysts, may accelerate the process by factors up to $10^7$ while preserving the inertness of both the azides and alkynes toward the vast majority of functional groups and conditions that may be present in vivo. Suitable copper catalyst which may be utilized include, but are not limited to, copper sulfate, copper iodide, copper (II) sulfate in combination with ascorbic acid, combinations thereof, and the like. In embodiments, the copper catalyst may include copper sulfate, in embodiments, $CuSO_4$, $5H_2O$.

The amount of catalyst needed may depend upon the starting materials utilized and their degree of functionalization. In embodiments, a suitable amount of catalyst may be from about 1% to about 10% by weight, in embodiments from about 2% to about 5% by weight.

In embodiments, a buffer salt may be combined with the above catalyst. Such buffers include, but are not limited to, acetates, citrates, malonates, tartarates, succinates, benzoates, ascorbates, phosphates, sulfates, nitrates, bicarbonates, carbonates, combinations thereof, and the like. In embodiments, ascorbates such as sodium ascorbate, calcium ascorbate, iron (II) ascorbate, combinations thereof, and the like, may be utilized with the catalyst.

The compounds produced from the above copper catalyzed reaction, which may be azoles, may be utilized to form bioadhesives of the present disclosure.

In embodiments, the first component, the second component, or both, may incorporate additional functional groups. Such additional functional groups include, but are not limited to, amino, alkoxy, carboxylic acids, carboxylic esters, ketones, ethers, amides, sulfones, sulfonamides, combinations thereof, and the like. In embodiments, the use of a first or second component that also possesses amine functionality may be useful, as amines may be beneficial to the copper-catalyzed process by providing a basic environment which assists in the production of Cu-acetylide intermediates. The amines may also contribute to productive chelating interactions with the metal center, for example, the amines may provide an important component of triazolylamine ligands for Cu(I), at least one example of which may include enhanced catalytic efficiencies in solution-phase reactions.

In embodiments, the ratio of azide to alkyne in forming a bioadhesive composition of the present disclosure may be from about 1:2 to about 1:1, in embodiments about 1:1.

In embodiments the first component, the second component, the catalyst, or any combination thereof, may be in a dilute solution. Suitable solvents which may be utilized to form a dilute solution include any biocompatible solvents within the purview of those skilled in the art which will not interfere with the reaction of the azide groups of the first component with the alkyne groups of the second component. Suitable solvents which may be utilized include, for example, polar solvents such as water, ethanol, triethylene glycol, dimethyl sulfoxide (DMSO), glymes (such as diglyme, triglyme, tetraglyme, and the like), polyethylene glycols, methoxy-polyethylene glycols, dimethylformamide, dimethylacetamide, gamma-butyrolactone, N-methylpyrollidone (NMP), ketones such as methyl ethyl ketone, cyclohexanone, diethylene glycol monoethyl ether acetate, diethylene glycol monobutyl ether acetate, diethylene glycol monomethyl ether, diethylene glycol monoethyl ether, diethylene glycol monobutyl ether, diethylene glycol monoisobutyl ether, diisobutyl ketone, diacetone alcohol, ethyl amyl ketone, ethyl lactate, and the like. In other embodiments, solvents such as tetrahydrofuran, ethyl acetate, isopropyl acetate, butyl acetate, isopropanol, butanol, acetone, and the like, may be utilized. In embodiments, combinations of any of the foregoing solvents may be utilized to form a dilute solution.

A solvent may be mixed with the first component, the second component, the catalyst, or any combination thereof. A solvent may be mixed with the first component so that the first component is at a concentration of from about 5 weight percent to about 50 weight percent of the dilute solution, in embodiments from about 8 weight percent to about 20 weight percent of the dilute solution. A solvent may be mixed with the second component so that the second component is at a concentration of from about 5 weight percent to about 50 weight percent of the dilute solution, in embodiments from about 8 weight percent to about 20 percent of the dilute solution. A solvent may be mixed with the catalyst so that the catalyst is at a concentration of from about 10 weight percent to about 80 weight percent of the dilute solution, in embodiments from about 30 weight percent to about 50 weight percent of the dilute solution.

The mixture of the first component, second component, catalyst, and any solvent as described herein may result in an emulsion or a diluted solution. The viscosity of the resulting emulsion or solution may be from about 1 cP to about 50 cP, in other embodiments from about 2 cP to about 10 cP, in still other embodiments from about 3 cP to about 5 cP.

The amount of solvent used will depend on a number of factors including the particular first component, second component, catalyst, or combination thereof that are to be employed and the intended end use of the composition.

In accordance with the present disclosure, the rate of curing of a composition of the present disclosure may be tailored by controlling the concentration of the first component, the second component, the catalyst, or any combination thereof. Generally, a faster cure time may be observed at a higher concentration of either the first or second component or catalyst than the rate observed for the same component at a lower concentration. Compositions of the present disclosure may cure from about 1 second to about 5 minutes after the two components are contacted with a catalyst and applied to tissue, in embodiments from about 30 seconds to about 2.5 minutes after contact.

A variety of optional ingredients may also be added to the compositions of the present disclosure including, but not limited to, surfactants, antimicrobial agents, colorants, preservatives, imaging agents e.g., iodine or barium sulfate, or fluorine, or medicinal agents. In some embodiments, the present compositions may optionally contain one or more bioactive agents. The term “bioactive agent”, as used herein, is used in its broadest sense and includes any substance or mixture of substances that have clinical use. Consequently, bioactive agents may or may not have pharmacological activity per se, e.g., a dye. Alternatively, a bioactive agent could be any agent which provides a therapeutic or prophylactic effect, a compound that affects or participates in tissue growth, cell growth, and/or cell differentiation, a compound that may be able to invoke a biological action such as an immune response, or could play any other role in one or more biological processes.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Suitable antimicrobial agents which may be included as a bioactive agent in the present compositions include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine or rh-lactoferrin and lactoferricin B may be included as a bioactive agent in the present compositions.

Other bioactive agents which may be included as a bioactive agent in the present compositions include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the present compositions include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

Naturally occurring polymers, including proteins such as collagen and derivatives of various naturally occurring polysaccharides such as glycosaminoglycans, can optionally be incorporated into the compositions of the present disclosure as a bioactive agent.

A single bioactive agent may be utilized in the present compositions or, in alternate embodiments, any combination of bioactive agents may be utilized in the present compositions.

The azide groups on the first component and alkyne groups on the second component described above permit the present compositions to cross-link to form a gel matrix that serves as an excellent tissue adhesive or sealant upon administration to tissue. Normally, the cross-linking reaction may be conducted at temperatures of from about 20° C. to about 40° C., in embodiments from about 25° C. to about 37° C. The exact reaction conditions for achieving cross-linking of the compositions of the present disclosure depend upon a variety of factors, including the functionality of the components, the degree of endcapping, the degree of functionalization, the selection of catalyst and amount utilized, the particular solvent, if any, and the like.

Where the composition of the present disclosure is intended for delivery of a drug or protein, the amounts of the first and second components can be adjusted to promote the initial retention of the drug or polymer in the bioadhesive composition and its subsequent release. Methods and means for making such adjustments will be readily apparent to those skilled in the art.

The first component, optionally in solution, the second component, also optionally in solution, and the catalyst, also optionally in solution, may be utilized to form an adhesive and/or sealant of the present disclosure, sometimes referred to herein as a bioadhesive composition, by combining the components utilizing any method within the purview of those skilled in the art, including mixing, blending, dripping, brushing, and the like, or any other direct manipulation of the compositions on the tissue surface, or spraying of the compositions onto the surface. In open surgery, application by hand, forceps or the like is contemplated. In endoscopic surgery, the compositions can be delivered through the cannula of a trocar, and spread at the site by any device known in the art.

For example, in some embodiments the first component with azide groups and the second component with alkyne groups in dilute solution may be combined with a catalyst using mixing with a simple device such as a spatula. In other embodiments, the first component and the second component in dilute solution may be combined by simply placing the two components into a first syringe and expelling the contents of the first syringe into a second syringe, followed by expelling the contents of the second syringe into the first syringe, and repeating this process between the two syringes until the components are mixed. In such an embodiment, the catalyst may be included in the first syringe, the second syringe, or both.

Thus, in some embodiments, the first component and the second component in dilute solution may be combined with a catalyst, in embodiments a copper catalyst, prior to administration. This may be advantageous where the compositions of the present disclosure are to be utilized as a void filler or sealant to fill a defect in an animal's body, in order to more precisely control the conditions and extent of cross-linking. For example, it may be desirable to partially cross-link the composition prior to use to fill a void in animal tissue. In such a case a bioadhesive composition of the present disclosure can be applied to the void or defect and allowed to set, thereby filling the void or defect.

In other embodiments, the first component may be combined with the second component and catalyst, optionally in dilute solution, at the time of administration. One example includes keeping the first component separate from the second component, and spraying the individual ingredients and the catalyst in a consecutive manner onto the same location, thereby allowing the two ingredients and catalyst to mix and form a bond in situ. In this example, the catalyst may be kept separate from the two components, kept with the first component, kept with the second component, or kept with both components, and will catalyze the reaction of the first component and second component upon application of the catalyst with the two components.

Another example includes keeping the first component separate from the second component and spraying the two ingredients and catalyst simultaneously through the same device such as a sprayer or nozzle, thereby allowing the ingredients to mix while being sprayed onto tissue, at which time they will form a bond in situ.

Methods for combining the two components and catalyst at the time of administration are within the purview of those skilled in the art and include, for example, dispensing the two components and catalyst from a conventional adhesive dispenser, which typically provides mixing of the first and second components with catalyst prior to the dispenser. Such dispensers are disclosed, for example, in U.S. Pat. Nos. 4,978,336, 4,361,055, 4,979,942, 4,359,049, 4,874,368, 5,368,563, and 6,527,749, the entire disclosures of each of which are incorporated by reference herein.

The compositions of the present disclosure can be used for a number of different human and animal medical applications including, but not limited to, wound closure (including surgical incisions and other wounds). Adhesives may be used to bind tissue together either as a replacement of, or as a supplement to, sutures, staples, clamps, tapes, bandages, and the like. Use of the present compositions can eliminate or substantially reduce the number of sutures normally required during current practices, and eliminate the subsequent need for removal of staples and certain types of sutures. The compositions described herein can thus be suitable for use with delicate tissues where sutures, clamps or other conventional tissue closure mechanisms may cause further tissue damage. For example, the compositions of the present disclosure may be used to seal or adhere delicate tissue together, such as lung tissue, in place of conventional tools that may cause mechanical stress. The present compositions can also be used to seal air and/or fluid leaks in tissue as well as to prevent post-surgical adhesions and to fill voids and/or defects in tissue.

To effectuate the joining of two tissue edges, the two edges may be approximated, and a composition of the present disclosure may be applied to the two approximated edges. In embodiments, the first component, second component and catalyst may first be combined to form a bioadhesive composition, which may then be applied to tissue. A second tissue surface may then be contacted with the tissue possessing the bioadhesive composition so that it adheres thereto. In other embodiments, the first component, second component, and catalyst may be separately applied to a tissue surface, a second tissue surface may then be contacted with the first tissue surface, and a bioadhesive composition may then form adhering the two tissue surfaces. In other embodiments, the first component, second component and catalyst may be separately applied to at least two tissue surfaces, and the tissue surfaces may then be contacted with each other so that a bioadhesive composition of the present disclosure forms in vivo to adhere the tissue surfaces.

The bioadhesive composition of the present disclosure crosslinks rapidly, generally taking less than one minute. Compositions of the present disclosure can thus be applied to the wound and allowed to set, thereby closing the wound.

The compositions described herein can also be used as sealants. When used as a sealant, a composition of the present disclosure can be used in surgery to prevent or inhibit bleeding or fluid leakage both during and after a surgical procedure. It can also be applied to prevent air leaks associated with pulmonary surgery. Compositions herein may be applied directly to the desired area in at least an amount sufficient to seal off any defect in the tissue and seal off any fluid or air movement. The compositions may also be used to prevent or control blood or other fluid leaks at suture or staple lines.

The present compositions also can be used to attach skin grafts and position tissue flaps during reconstructive surgery. Alternatively, the present compositions can be used to close tissue flaps in periodontal surgery.

In another embodiment, the present disclosure is directed to a method for using compositions of the present disclosure to adhere a medical device to tissue. Suitable medical devices include implants. Other medical devices include, but are not limited to, pacemakers, stents, shunts and the like. Generally, for adhering a device to the surface of animal tissue, a composition of the present disclosure can be applied to the device, to the tissue surface or to both. The device and tissue surface are then brought into contact with the present composition therebetween. In other embodiments the first component may be applied to the device or tissue surface, and the second component applied to the other. The device and tissue surface are brought into contact with each other, so that the first component and second component are in contact with each other. Application of the catalyst will result in formation of a composition of the present disclosure. Once the composition crosslinks and sets, the device and tissue surface are effectively adhered to each other.

The present compositions can also be used to prevent post surgical adhesions. In such an application, a composition of the present disclosure may be applied and cured to form a layer on surfaces of internal tissues in order to prevent the formation of adhesions at a surgical site during the healing process.

The resulting bioadhesive compositions have a number of advantageous properties. The bioadhesive compositions of the present disclosure are safe, possess enhanced adherence to tissue, are biodegradable, have enhanced hemostatic potential, have low cost, and are easy to prepare and use. By varying the selection of the compounds utilized to form the bioadhesive composition, the strength and elasticity of the bioadhesive composition can be controlled, as can the gelation time.

Adhesives and/or sealants formed with bioadhesive compositions of the present disclosure possess excellent strength and similar physical properties. The compositions herein rapidly form a compliant gel matrix, which insures stationary positioning of tissue edges or implanted medical devices in the desired location and lowers overall required surgical/application time. The composition forms strong cohesive bonds. It exhibits excellent mechanical performance and strength, while retaining the necessary pliability to adhere living tissue. This strength and pliability allows a degree of movement of tissue without shifting the surgical tissue edge.

The following Examples are being submitted to illustrate embodiments of the present disclosure. These Examples are intended to be illustrative only and are not intended to limit the scope of the present disclosure. Also, parts and percentages are by weight unless otherwise indicated.

EXAMPLE 1

A tosylate was prepared for use in synthesizing an azide. About 10 mL of tetrahydrofuran (THF) was added to a solution of about 3.6 grams (about 5 mmoles) pentaerythritol ethoxylate and about 1.45 grams sodium hydroxide (about 36 mmoles) in about 10 mL of water. Pentaerythritol ethoxylate (sometimes referred to herein as pentaerythritol-EO) has the following structure:

(XX)

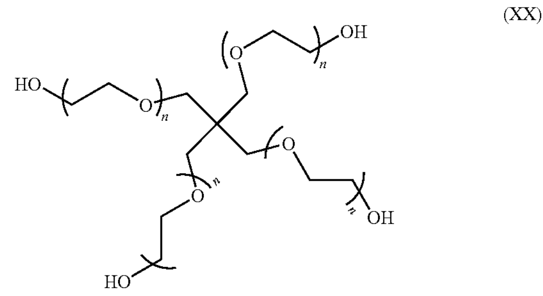

wherein n is from about 3 to about 60, in embodiments from about 4 to about 8.

About 4.31 grams (about 23 mmoles) of solid p-toluenesulfonyl chloride (p-Tos-Cl) was then added to the above solution at room temperature (about 21±5° C.) under a nitrogen atmosphere for about 24 hours. The reaction mixture was then diluted with about 30 mL of water and extracted 4 times with 40 mL of ethyl acetate. The organic phase was dried over magnesium sulfate, filtered, evaporated and dried under high vacuum. The resulting product was analyzed by proton NMR in deuterated chloroform. Treatment of the NMR sample with trichloroacetyl isocyanate showed that the final product had about 16% of free hydroxyl groups.

The polysulfonate thus produced, which may be referred to herein as pentaerythritol tosylate (pentaerythritol-Tos) was as follows:

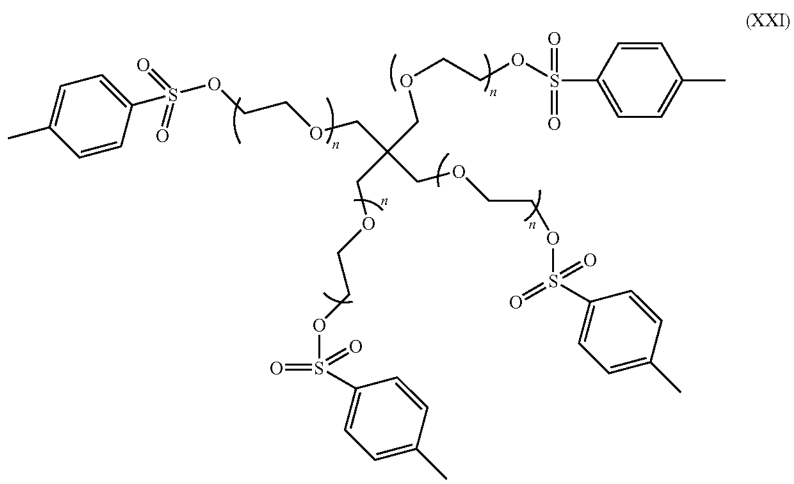

wherein n is a number from about 3 to about 60, in embodiments from about 4 to about 8.

EXAMPLE 2

A 4-arm azide was prepared for a click reaction with a polyacetylene. About 2.76 grams (about 2 mmoles) of the pentaerythritol-Tos polysulfonate prepared in Example 1 above was reacted with about 0.57 grams (about 9 mmoles) of sodium azide ($NaN_3$) in about 10 mL of dimethyl formamide. The reaction mixture was stirred at about 60°C. under a nitrogen atmosphere. The reaction mixture was partitioned between about 15 mL of water and about 40 ml of ether. The two phases were separated and the aqueous phase was extracted with about 25 mL of ether. The combined organic phase was dried over magnesium sulfate, filtered and evaporated. The residue was analyzed by NMR. The NMR spectrum confirmed the displacement of the tosylate groups.

The 4-arm azide thus produced was as follows:

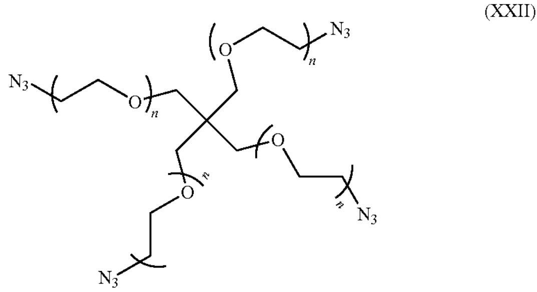

where n is a number from about 3 to about 60, in embodiments from about 4 to about 8.

EXAMPLE 3

An acetylenic derivative was prepared for use in a click reaction. About 15.75 grams (about 25 mmoles) of pentaerythritol propoxylate was slowly added to about 21.81 grams (about 125 mmoles) of 2,4-tolylene diisocyanate (TDI) at room temperature (about 21±5° C.). The mixture was then heated at about 65° C. for about 18 hours. The reaction mixture was washed seven times with petroleum ether. For each of the washings, about 45 mL of petroleum ether was added and the reaction mixture was stirred at about 65° C. for a period of time of from about 10 minutes to about 15 minutes. The mixture was decanted and the supernatant petroleum ether was removed with a pipette. The process was repeated six times; the resulting material was dried under a vacuum to provide a pentaerythritol propoxylate-TDI adduct. The material had a free isocyanate content of about 13.49%, as determined by titration. The pentaerythritol propoxylate-TDI adduct was of the formula depicted in FIG. 1, where n was from about 1 to about 15.

About 3.46 grams (about 13.49% free NCO) of this pentaerythritol propoxylate-TDI adduct was combined with about 3.83 grams (about 45 mmoles) of 4-pentyn-1-ol in about 6 mL of THF. The mixture was heated at about 65° C. under a nitrogen atmosphere for about 20 hours.

Figure 2:
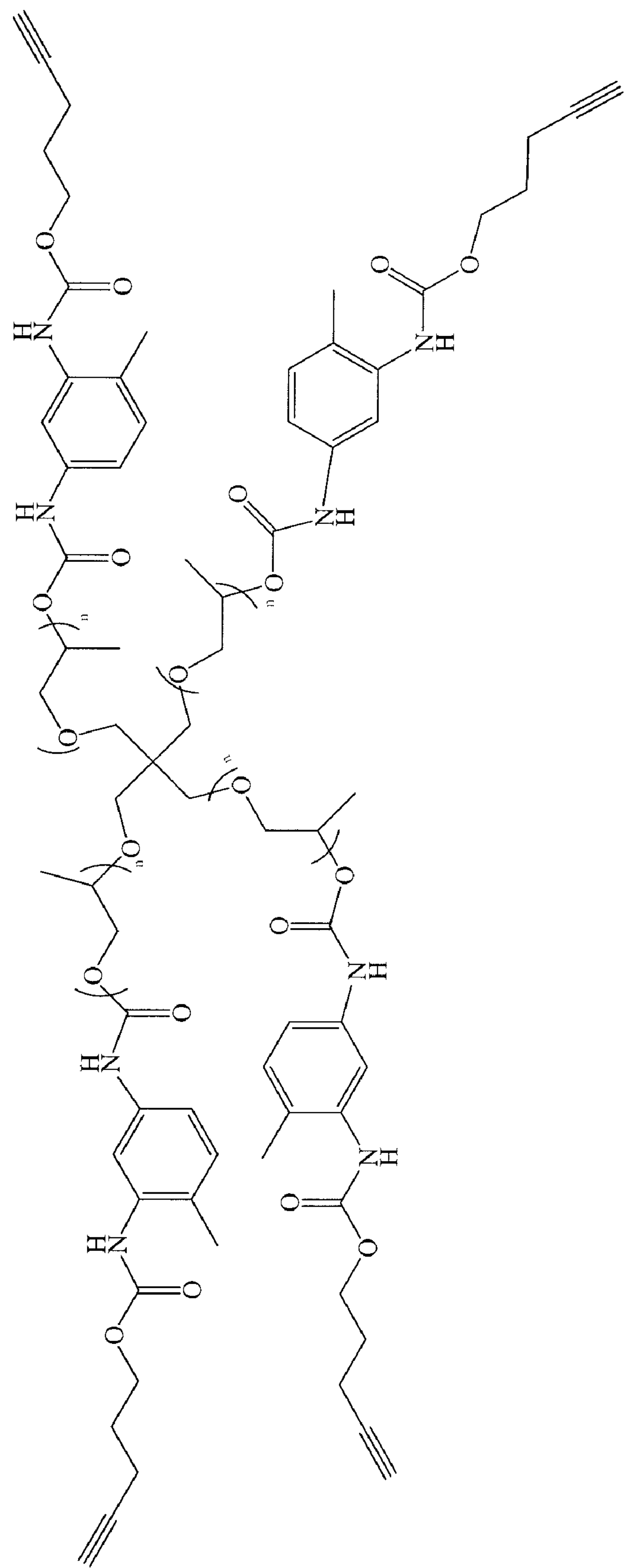
FIG. 2 is a depiction of an acetylenic derivative for use in forming a bioadhesive composition of the present disclosure.

The acetylenic derivative thus produced is depicted in FIG. 2, where n was from about 1 to about 15.

EXAMPLE 4

The 4-arm azide of Example 2 was combined with the acetylenic derivative of Example 3 to produce a composition of the present disclosure as follows. About 100 mg of the acetylenic derivative of Example 3 (about 68 μmoles) and about 1.7 mg (about 68 μmoles) of copper sulfate pentahydrate ($CuSO_4$,$5H_2O$) were dissolved in a mixture of THF and water (about 0.25 mL each) and mixed with a solution including about 68.6 mg (about 68 moles) of the 4-arm azide of Example 2 and about 5.4 mg of sodium ascorbate in a mixture of THF and water (about 0.25 ml each). The resulting mixture was shaken on a Vortex to produce a composition of the present disclosure.

It will be understood that various modifications may be made to the embodiments disclosed herein. Therefore the above description should not be construed as limiting, but merely as exemplifications of typical embodiments. Those skilled in the art will envision other modifications within the scope and spirit of the claims appended hereto.

What is claimed is:

1. A method for adhering tissue comprising:

contacting a first component possessing at least two alkyne groups with a second component selected from the group consisting of N—((2S,3R,4S,5S,6S)-4,5-diazido-6-(azidomethyl)-2-(benzyloxy)tetrahydro-2H-pyran-3- yl)acetamide, 4,4'-diazido-2,2'-stilbenedisulfonic acid disodium salt hydrate, (3R,4R,5S,6S)-4-azido-6-(azidomethyl)tetrahydro-2H-pyran-2,3,5-triol, 4,4'-oxybis (azidobenzene), 4,4'-sulfonylbis(azidobenzene), bis[2-(4-azidosalicylamido)ethyl]disulfide, 1,17-diazido-3,6,9,12,15-pentaoxaheptadecane, (2E,6E)-2,6-bis(4-azidobenzylidene)cyclohexanone, tetraazido-pentaerythritol ethoxylate, heptakis-6-azido-6-deoxy-beta-cyclodextrin, and combinations thereof;

catalyzing a polymerization of the first component and the second component to form a bioadhesive composition; and adhering the bioadhesive composition to at least one tissue surface.

2. The method according to claim 1, wherein the first component comprises a core comprising a polyol having at least 2 functional groups.

3. The method according to claim 2, wherein the polyol is selected from the group consisting of polyethers, polyesters, polyether-esters, polyalkanols, and combinations thereof.

4. The method according to claim 2, wherein the polyol comprises a polyether selected from the group consisting of polyethylene glycol, polypropylene glycol, polybutylene glycol, polytetramethylene glycol, polyhexamethylene glycol, cyclodextrin-polyethylene glycols, polyacetals, and combinations thereof.

5. The method according to claim 2, wherein the polyol comprises a polyester selected from the group consisting of trimethylene carbonate, ϵ-caprolactone, p-dioxanone, glycolide, lactide, 1,5-dioxepan-2-one, polybutylene adipate, polyethylene adipate, polyethylene terephthalate, and combinations thereof.

6. The method according to claim 2, wherein the polyol comprises a poly(ether-ester) block.

7. The method according to claim 1 wherein the first component has at least 2 arms.

8. The method according to claim 1, wherein the first component comprises a core comprising a polyrotaxane.

9. The method according to claim 1, wherein the first component is of a formula selected from the group consisting of

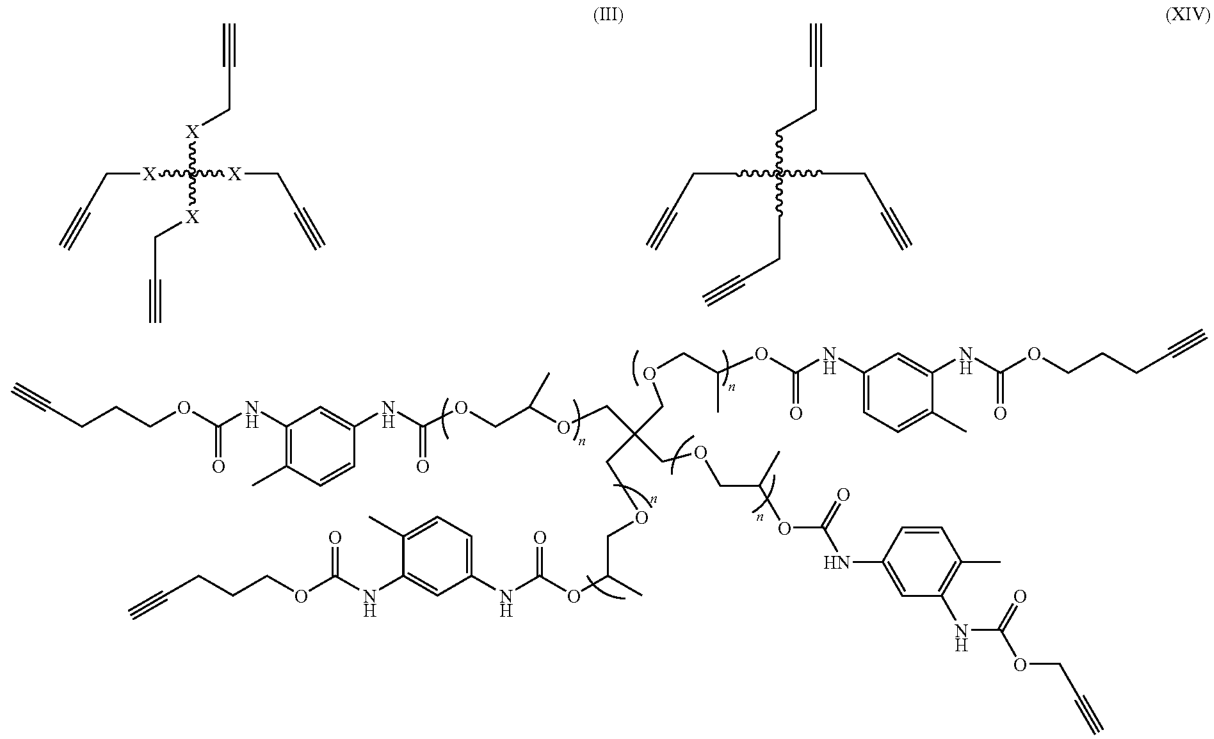

wherein X is selected from the group consisting of O, NH, S, $SO_2$, and combinations thereof and n is a number from about 1 to about 15.

10. The method according to claim 1, wherein the polymerization of the first component and the second component is catalyzed by a copper catalyst selected from the group consisting of copper sulfate, copper iodide, and combinations thereof.

11. The method according to claim 10, wherein the copper catalyst is contacted with a buffer salt selected from the group consisting of acetates, citrates, malonates, tartarates, succinates, benzoates, ascorbates, phosphates, sulfates, nitrates, bicarbonates, carbonates, and combinations thereof.

12. The method according to claim 1, wherein the first component possesses additional functional groups selected from the group consisting of amino, alkoxy, carboxylic acids, carboxylic esters, ketones, ethers, amides, sulfones, sulfonamides, and combinations thereof.

13. The method according to claim 1, wherein the ratio of azide groups from the second component to alkyne groups from the first component is from about 1:2.

14. The method according to claim 1, wherein the first component, optionally the second component, and optionally the catalyst, are in a solution.

15. The method according to claim 1, wherein the bioadhesive composition is formed prior to application to tissue.

16. The method according to claim 1, wherein the bioadhesive composition is formed in vivo.

17. The method according to claim 1, wherein the bioadhesive composition is of the following formula:

(XIII)

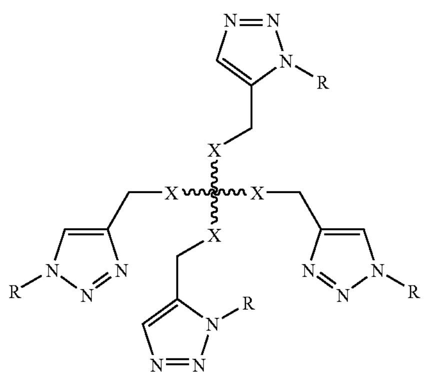

wherein X is selected from the group consisting of O, NH, S, $SO_2$, and combinations thereof, and R comprises the remainder of the second component.

18. The method according to claim 1, wherein the bioadhesive composition further comprises at least one bioactive agent.

19. The method according to claim 1, further comprising contacting the bioadhesive composition with a second tissue surface.

20. The method according to claim 1, further comprising contacting the bioadhesive composition with an implant.

21. A method for adhering tissue comprising:

contacting a first component possessing at least two alkyne groups with a second component possessing at least two azide groups;

catalyzing a polymerization of the first component and the second component to form a bioadhesive composition; and contacting the bioadhesive composition to at least one tissue surface so that the bioadhesive composition adheres to the at least one tissue surface, wherein the first component and optionally the second component comprises a core comprising a polyol comprising a poly(ether-ester) block having at least about 2 functional groups.

22. A method for adhering tissue comprising:

contacting a first component possessing at least two alkyne groups with a second component possessing at least two azide groups;

catalyzing a polymerization of the first component and the second component to form a bioadhesive composition; and contacting the bioadhesive composition to at least one tissue surface so that the bioadhesive composition adheres to the at least one tissue surface, wherein the first component and optionally the second component comprises a core comprising a polyrotaxane.

* * * * *